United States Patent
Misawa et al.

(10) Patent No.: US 7,265,848 B2
(45) Date of Patent: Sep. 4, 2007

(54) TIME-RESOLVED NONLINEAR COMPLEX SENSITIVITY MEASURING APPARATUS

(75) Inventors: Kazuhiko Misawa, Tokyo (JP); Fumikazu Inuzuka, Kanagawa (JP); Hiroyoshi Lang, Tokyo (JP)

(73) Assignee: Japan Science and Technology, Saitama (JP)

( * ) Notice: Subject to any disclaimer, the term of this patent is extended or adjusted under 35 U.S.C. 154(b) by 291 days.

(21) Appl. No.: 10/528,140

(22) PCT Filed: Sep. 19, 2003

(86) PCT No.: PCT/JP03/12015

§ 371 (c)(1),
(2), (4) Date: Mar. 17, 2005

(87) PCT Pub. No.: WO2004/027399

PCT Pub. Date: Apr. 1, 2004

(65) Prior Publication Data

US 2006/0033930 A1  Feb. 16, 2006

(30) Foreign Application Priority Data

Sep. 20, 2002 (JP) ............................. 2002-276155
Jan. 7, 2003 (JP) ............................. 2003-001549

(51) Int. Cl.
*G01B 9/02* (2006.01)
(52) U.S. Cl. .................................... 356/483
(58) Field of Classification Search ................ 356/483, 356/459, 460, 464, 463, 462, 461
See application file for complete search history.

(56) References Cited

U.S. PATENT DOCUMENTS 6,831,749 B2* 12/2004 Ohno et al. .................. 356/483

FOREIGN PATENT DOCUMENTS

JP  2001-194268  7/2001

OTHER PUBLICATIONS

Fumikazu Inuzuka et al.; The Japan Society of Applied Physics, vol. 63rd, No. 3, Sep. 24, 2002, p. 941, 26a-YC-10. Cited in the int'l. search rpt.

* cited by examiner

*Primary Examiner*—Hwa (Andrew) Lee
(74) *Attorney, Agent, or Firm*—Westerman, Hattori, Daniels & Adrian, LLP.

(57) ABSTRACT

A time resolved, nonlinear complex susceptibility measuring apparatus (1) that is capable of measurement unaffected by any distortion of the wave front of a probe light whereby a temporal change in the nonlinear complex susceptibility of a nonlinear optical material that occurs when it is irradiated with a light pulse in a femtosecond range is measured using a pair of polarized lights orthogonal to each other which are formed by splitting a single light pulse into a reference and a probe light (5) and (6) in a polarized light splitting Sagnac type interference light path (8). A direction of polarization converting mechanism for rotating a direction of polarization of the reference and probe lights by an angle of 90° in the polarized light splitting Sagnac type interference light path is included to align the directions of polarization on a test specimen (3). A phase difference between the reference and probe lights which are output from the polarized light splitting Sagnac type interference light path is swept by a phase difference sweep mechanism (9) whereby a time resolved, nonlinear complex susceptibility is found from a phase difference sweep interference waveform obtained by measuring the intensity of interference light between the reference and probe lights for each of such phase differences swept.

6 Claims, 10 Drawing Sheets

λ/2 Wavelength plate (b)

λ/4 Wavelength plate

λ/4 Wavelength plate (b)

Polarizer

Wavelength (nm)

TIME-RESOLVED NONLINEAR COMPLEX SENSITIVITY MEASURING APPARATUS

TECHNICAL FIELD

The present invention relates to a time resolved, nonlinear complex susceptibility measuring apparatus for measuring a change with time by relaxation of a nonlinear polarization induced in a material.

BACKGROUND ART

Next-generation optical information transmission systems require ultrafastness, large capacity and parallel processability. Especially, the femtosecond pulse generating technique rapidly growing in recent years are indicated to be capable of processing information at a speed faster by three figures than the conventional optical information transmission techniques. In putting femtosecond optical communication to practical use, however, there remain problems that cannot be solved only by the femtosecond region pulse generating technique. While band problems in fiber optic transmission lines are important, the problem considered the most acute is to develop a device which can shape, modulate, demodulate and switch ultrashort light pulses at an ultrahigh speed that is commensurate with the width of a femtosecond pulse. Such an ultrafast device cannot be realized in the form of an electronic device but as an optical device designed to control light by light. Further, optimum is to use light phase modulation rather than light intensity modulation in order to make modulation unaffected by a transmission loss.

In order to realize optical phase modulated communication, a phase demodulating device is also important, which may, for example, embody by an up-conversion frequency generation method using a nonlinear optical material as proposed in a light multiplex transmitter-receiver by the present inventors (see Japan Patent Application No. 2001-268846, pages 19-21 and FIGS. 8-10). This method utilizes the up-conversion frequency generation by a nonlinear optical crystal to read phase information from femtosecond light pulses.

Significant progress in study of nonlinear optical effects in recent years has lead to development of optical materials that exhibit large nonlinear properties. However, realizing a phase demodulating device requires precisely assessing not only the magnitude of a nonlinear optical constant but also how such nonlinear properties relax in a femtosecond region. Unfortunately, the conventional methods do not allow measuring ultrafast temporal changes of a nonlinear property in a temporal resolution in a femtosecond region.

In view of the above problem in the prior art, the present invention seeks to provide a time resolved, nonlinear complex susceptibility measuring apparatus that is capable of assessing the performance of a nonlinear optical material for direct use in ultrafast optical communication techniques, namely of precisely measuring not only the magnitude of a nonlinear optical constant of an optical material but also an ultrafast change with time of a nonlinear complex susceptibility of the optical material in a femtosecond region.

Mention is here made of problems that arise in connection with a conventional time resolved, nonlinear complex susceptibility measuring apparatus. A Sagnac interferometric light path comprises a beam splitter serving as both an input and an out end, and a plurality of mirrors disposed so that a pair of split light beams from the beam splitter travel through an identical closed optical path while turning clockwise and counterclockwise, respectively, therethrough and then return to the beam splitter. If in this light path a test specimen is disposed at a position such that to reach it the two light beams have distances of travel different by an appropriate length, it is then possible to make an appropriate difference in time position between the two light beams passing the test specimen. Then, irradiating the test specimen with a light pulse within this time interval allows a reference light and a probe light to pass the test specimen before and after it is irradiated with a light pulse, respectively.

Light passing through a test specimen in which a nonlinear polarization is created is affected by its nonlinear complex susceptibility and then changes in phase and amplitude. It follows, therefore, that interference between the reference and probe lights outgoing from the Sagnac interferometric light path reflects a nonlinear complex susceptibility of such a test specimen, and measuring this interference allows determining the nonlinear complex susceptibility. Further, if the measurement is made while continuously varying the timing at which a test specimen is irradiated with a light pulse, it is then possible to determine a nonlinear complex susceptibility during the light pulse irradiation and that after the same in its relaxation state, namely time resolved, nonlinear complex susceptibilities.

Figure 7:
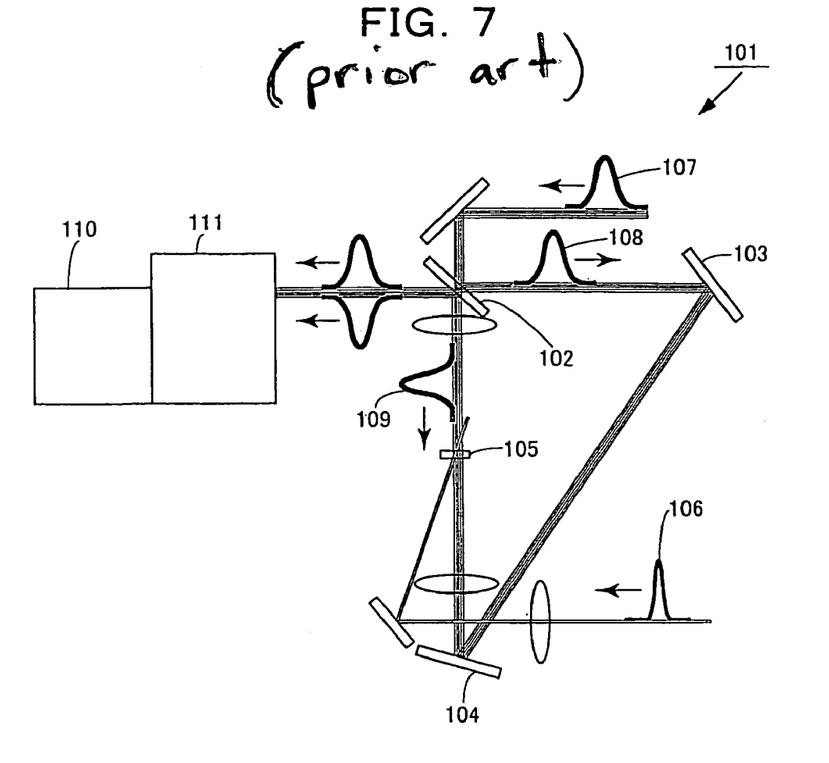
FIG. 7 is a diagram illustrating the makeup of a conventional time resolved, nonlinear complex susceptibility measuring apparatus of Sagnac interferometer type.

FIG. 7 is a diagram illustrating the makeup of the conventional time resolved, nonlinear complex susceptibility measuring apparatus of Sagnac interferometer type. In the diagram, a Sagnac interferometer 101 has its light path made up of a beam splitter 102 and mirrors 103 and 104. A test specimen 105 is disposed near the beam splitter 102 in the light path and is irradiated with an excitation light pulse 106. A light pulse 107 supplied to the Sagnac interferometer 101 is split by the beam splitter 102 into a probe light 108 and a reference light 109 which propagate through the light path clockwise and counterclockwise as shown in the diagram, respectively.

Figure 8:
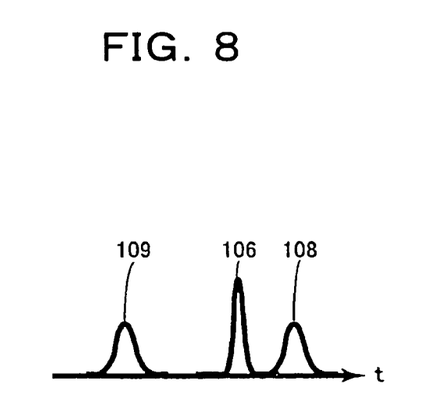
FIG. 8 is a chart illustrating the timings at which a probe light and a reference light pass the test specimen in the apparatus in which time is represented by its abscissa axis.

FIG. 8 is a chart illustrating the timings at which the probe light and the reference light pass the test specimen in which time is represented by its abscissa axis. With different lengths between clockwise and counterclockwise optical paths to the test specimen 105, the reference light 109 will reach first and the probe light 108 will reach later the specimen 105. The test specimen 105 is irradiated with the excitation light pulse 106 in a time period after the reference light pulse 109 reaches and before the probe light pulse 108 reaches the test specimen 105. In this time period, it is possible to continuously change the timing of irradiation with the excitation light pulse 106. Before reaching the beam splitter 102 shown in FIG. 7, the probe light 108 passes through the test specimen 105 immediately after it is excited by the excitation light pulse 106 and therefore has its phase and amplitude varied by a change in nonlinear complex susceptibility of the test specimen 105 caused by the excitation light pulse 106. On the other hand, the reference light 109 passes through the test specimen 105 that is unexcited by the excitation light pulse 106 and therefore reaches the beam splitter 102 without having the phase change and amplitude change of the test specimen. Since the clockwise and counterclockwise running optical paths are equivalent to each other, the probe light 108 and the reference light 109 when they leave the beam splitter 102 only differ in phase and amplitude by changes produced corresponding to those in the nonlinear complex susceptibility of the test specimen 105 caused by its excitation by the excitation light pulse 106.

Figure 9:
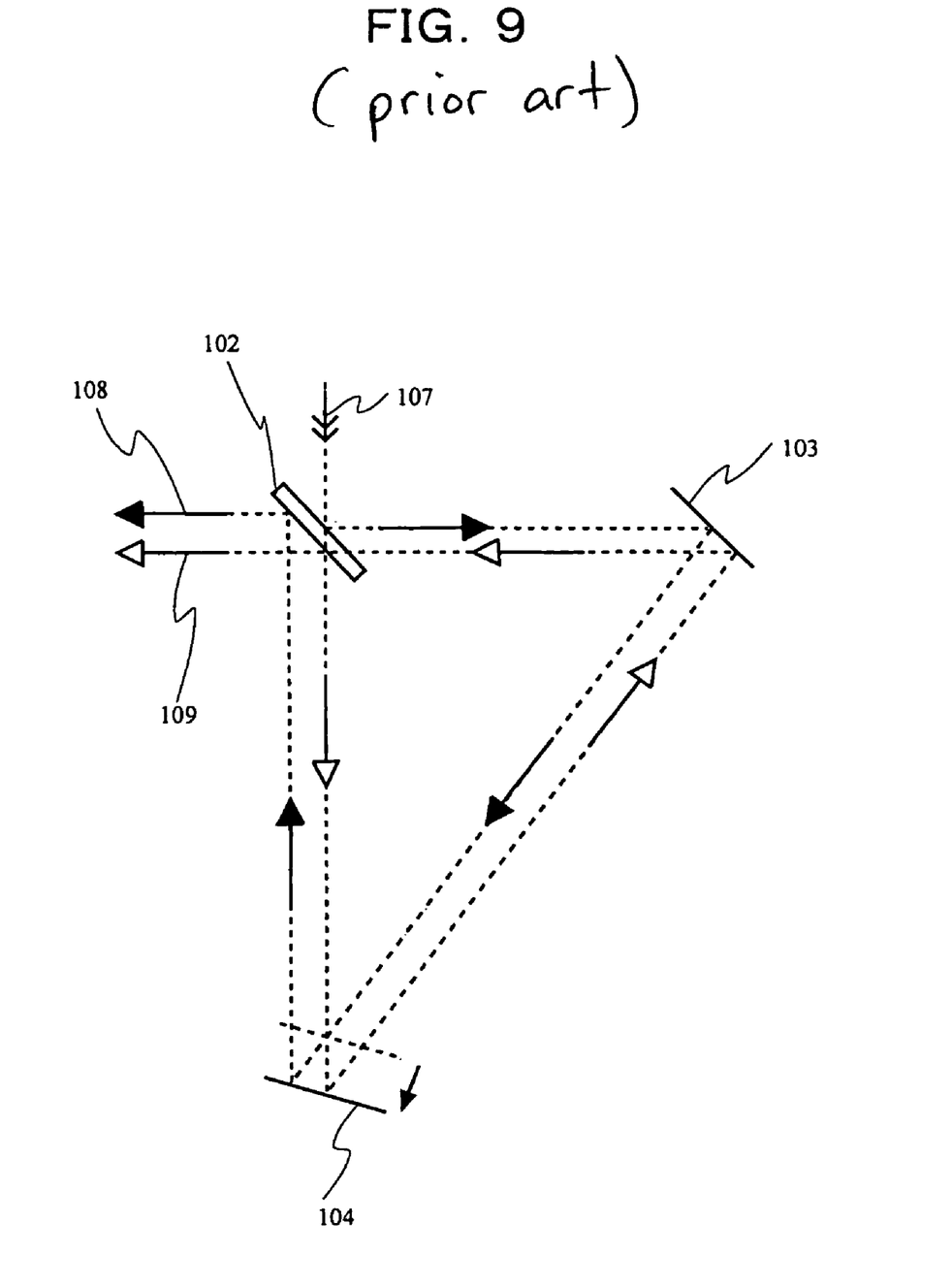
FIG. 9 is a diagram illustrating one conventional method of interfering probe light with reference light.

FIG. 9 is a diagram illustrating one conventional method of causing a probe light to interfere with a reference light. As shown in the Figure, the mirror 103 or 104 is shifted from its regular mirror position in the Sagnac interferometer to shift the clockwise optical path for the probe light 108 and the counterclockwise optical path for the reference light 109. Then, the curvatures of beam fronts of the probe light 108 and the reference light 109 may be utilized to cause them interfere and form their spatial interference fringes on the plane of a CCD camera 110 shown in FIG. 7. Alternatively, a white light source may be used to produce a light pulse 107 with which the Sagnac interferometer 101 is supplied and a spectroscope 111 may be disposed to form on the plane of the two-dimensional CCD camera 110 interference fringes for each of wavelengths dispersed.

Figure 10:
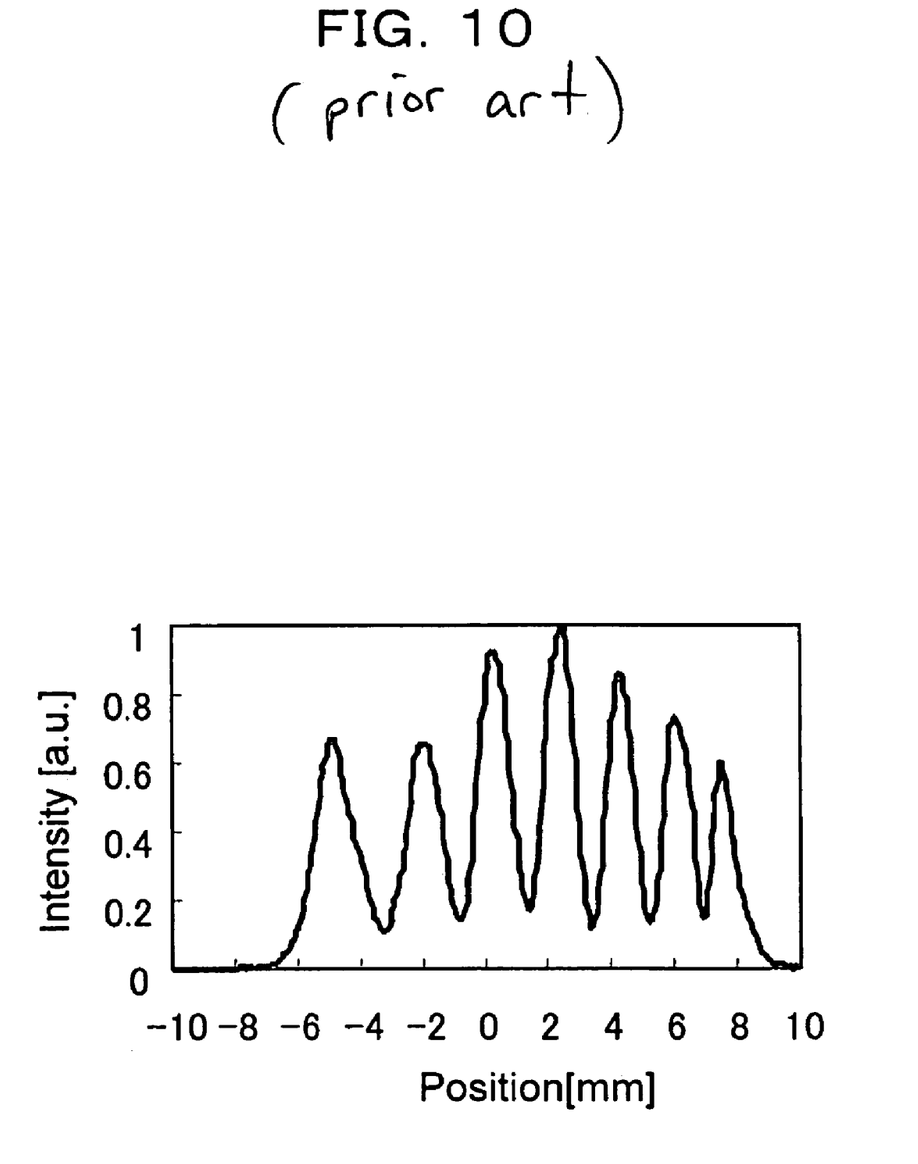
FIG. 10 is a graph illustrating spatial interference fringes according to the conventional time resolved, nonlinear complex susceptibility measuring apparatus of Sagnac interferometer type.

FIG. 10 is a diagram illustrating spatial interference fringes according to the conventional time resolved, nonlinear complex susceptibility measuring apparatus of Sagnac interferometer type wherein the abscissa axis represents the position of the CCD camera. A difference in phase between the probe light and the reference light produced by irradiating the test specimen with the excitation light pulse can be found by measuring a deviation of peaks of interference fringes when such a difference in phase is produced between the probe light and the reference light by irradiating the test specimen with the excitation light pulse from peaks of interference fringes where there is no difference in phase between the probe light and the reference light. This diagram shows interference fringes when a difference in phase is produced between the probe light and the reference light by irradiating the test specimen with the excitation light pulse. As can be seen from the diagram, the interference fringes are shorter in period when the position is positive and are longer in period when the position is negative and are thus asymmetrical in period about the position of 0 mm. This phenomenon arises due to the fact that an equiphase wave surface is bent by the probe light passing through an excited test specimen, i.e., the phase of the probe light in a cross section perpendicular to its beam axis fluctuates. The measurement of a difference in phase will be made theoretically possible when the interference fringes are of an ideal sine wave, and gives rise to a large error under the influence of a difference in period of interference fringes in the conventional method wherein a phase difference is to be found from a deviation in peaks of interference fringes.

Figure 11:
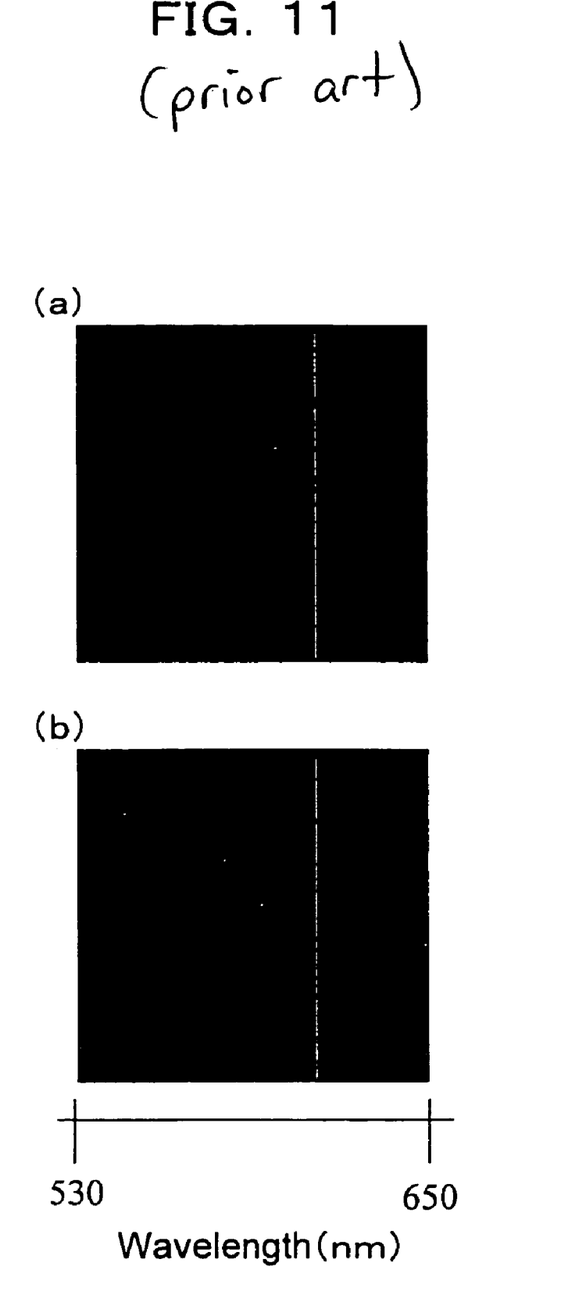
FIG. 11 illustrate results of measuring spatial interference fringes when a spectroscope is disposed to spatially disperse wavelengths in the conventional time, resolved, nonlinear complex susceptibility measuring apparatus of Sagnac interferometer type.

FIG. 11 has diagrams (a) and (b) illustrating results of measuring spatial interference fringes when a spectroscope is disposed to spatially disperse wavelengths in a conventional time, resolved, nonlinear complex susceptibility measuring apparatus of Sagnac interferometer type, in each of which diagrams the ordinate and abscissa axes correspond to a difference in optical path between a probe and a reference light and a light wavelength, respectively, and portions that appear white correspond to peaks of interference fringes. In FIG. 11 diagram (a) shows results of measurement when the test specimen is irradiated with no excitation light pulse and diagram (b) shows results of measurement when the test specimen is irradiated with an excitation light pulse. As shown in FIG. 11(*b*), there exist distortions in the interference fringes, which as in the case of FIG. 8 prevent a phase difference from being measured correctly.

Thus, a conventional time resolved, nonlinear complex susceptibility measuring apparatus of Sagnac interferometer type, in which optical paths for a probe and a reference light are shifted to form spatial interference fringes, has the problem that because of distortions it causes in the wave surface of probe light, it cannot measure a nonlinear complex susceptibility correctly.

As to the prior art to the present invention, reference is made to:

Y. Li, G. Eichmann and R. R. Alfano, "Pulsed-mode laser Sagnac interferometry with applications in nonlinear optics and optical switching", Applied Optics, Vol. 25, No. 2, p. 209 (1986);

R. Trebino and C. Hayden, "Antiresonant-ring transient spectroscopy", Optics Letters, Vol. 16, No. 7, p. 493 (1991);

M. C. Gabriel, N. A. Whitaker, Jr., C. W. Dirk, M. G. Kuzyk and M. Thakur, "Measurement of ultrafast optical nonlinearities using a modified Sagnac interferometer", Optics Letters, Vol. 16, No. 17, p. 1334 (1991);

K. Misawa and T. Kobayashi, "Femtosecond Sagnac interferometer for phasespectrophy", Optics Letters, Vol. 20, No. 14, p. 1550-1552 (1995); and D. H. Hurley and O. B. Wright, "Detection of ultrafast phenomena by use of a modified Sagnac interferometer", Optics Letters, Vol. 24, No. 18 (1999).

DISCLOSURE OF THE INVENTION

In view of the above, it is an object of the present invention to provide a time resolved, complex susceptibility measuring apparatus that is capable of measurement unaffected by any distortion in the wave surface of a probe light.

In order to achieve the objects mentioned above there is provided in accordance with the present invention a time resolved, nonlinear complex susceptibility measuring apparatus having: a Sagnac type interference light path in which a reference and a probe light to propagate, a light pulse light source for providing a light pulse with which to irradiate a test specimen disposed in the light path and for supplying the Sagnac type interference light path with a light pulse, and a measuring instrument for measuring the intensity of interference light between the reference and probe lights, characterized in that: the reference and probe lights are a pair of polarized lights orthogonal to each other, and the Sagnac type interference light path is a polarized light splitting Sagnac type interference light path, and that the apparatus includes: a direction of polarization converting mechanism for rotating a direction of polarization of the reference and probe lights in the polarized light splitting Sagnac type interference light path; a phase difference sweep mechanism for sweeping a phase difference between the reference and probe lights that are output from the polarized light splitting Sagnac type interference light path; and a phase difference compensating mechanism for compensating for a phase difference between the reference and probe lights, whereby a phase difference between the reference and probe lights that are output from the polarized light Sagnac type interference light path is swept and a time resolved, nonlinear complex susceptibility is found from a phase difference sweep interference waveform obtained by measuring the intensity of interference light between the reference and probe lights for each of such phase differences swept.

The said phase difference compensating mechanism for compensating for a phase difference between the reference and probe lights may comprise a $\lambda/2$ and a $\lambda/4$ wavelength plate disposed between the polarized light splitting Sagnac type interference light path and the light pulse light source for supplying the light path with the light pulse whereby rotating the $\lambda/2$ wavelength plate allows compensating for a phase difference between the reference and probe lights. The said direction of polarization converting mechanism for rotating a direction of polarization of the reference and probe lights by an angle of 90° in the polarized light splitting Sagnac type interference light path may comprise a λ/2 wavelength plate disposed in the light path. The said phase difference sweep mechanism for sweeping a phase difference between the reference and probe lights that are output from the polarized light splitting Sagnac type interference light path may comprise a λ/4 wavelength plate and a light polarizer which are disposed between an output end of the polarized light splitting Sagnac type interference light path and the measuring instrument for measuring the intensity of interference light between the reference and probe lights whereby rotating the λ/4 wavelength plate allows sweeping a phase difference between the reference and probe lights.

According to the apparatus makeup mentioned above, a linearly polarized light pulse emerging via a polarizer from a light pulse light source for supplying a polarized light splitting Sagnac type interference light path with light pulses enters a phase difference compensating mechanism. The phase difference compensating mechanism comprises a λ/2 wavelength plate that can be rotated as desired about its optical axis and a λ/4 wavelength plate having a fast or slow axis fixed to orient in a direction with an angle of 45° made with a direction of polarization of a reference or probe light as described below whereby rotating the λ/2 plate allows adjusting the phase difference between the reference and probe lights as desired. The phase difference compensating mechanism is used to compensate for and make zero any fixed phase difference that may be caused between the reference and probe lights when the reference or probe light is reflected or refracted by such as a polarized light beam splitter included as a part of the polarized light splitting Sagnac type interference light path.

The polarized light splitting Sagnac type interference light path comprises a plurality of mirrors and the polarized light beam splitter that serves also to provide a light input and a light output end. The polarized light beam splitter which at its reflecting surface reflects a light component having an electric field vector in a direction perpendicular to the light incident plane and transmits a light component having an electric field vector in a direction parallel to the light incident plane splits an elliptically polarized light whose fixed phase difference is compensated for by the phase difference compensating mechanism into a polarized light reflecting on the reflecting surface of the polarized light beam splitter and having an electric field vector perpendicular to an interference light path plane and a polarized light transmitted through the polarized light beam splitter and having an electric field vector parallel to the interference light path plane. These two polarized lights are used as a reference and a probe light or a probe and a reference light, respectively. The mirrors are disposed so that the two polarized lights split by the polarized light beam splitter propagate through the same light path and in mutually opposite directions, namely propagate clockwise and counterclockwise, to return to the polarized light beam splitter where they are again combined together into a single light beam.

A test specimen is disposed at a position in the polarized light splitting Sagnac type interference light path such that the clockwise optical path and the counterclockwise optical path differ in length by an appropriate difference of length so that there is an appropriate difference in time between the time instants at which the clockwise and counterclockwise traveling light beams pass the test specimen, respectively. Within this difference in time or time interval the test specimen is irradiated with a light pulse so that the reference and probe lights pass the test specimen before and after its irradiation with the light pulse, respectively. Thus, with the reference light unaffected and the probe pulse affected by a nonlinear complex susceptibility of the specimen, the reference and probe lights leaving the polarized light splitting Sagnac type interference light path have both a difference in phase and a difference in amplitude which reflects the nonlinear complex susceptibility of the test specimen.

Further, the polarized light splitting Sagnac type interference light path has a λ/2 wavelength plate disposed therein. Since the reference and probe lights propagate through the Sagnac type interference light path in mutually opposite directions, one of them reaches the test specimen after passing through the λ/2 wavelength plate and the other reaches the; λ/2 wavelength plate after passing through the test specimen. Thus, the reference and probe lights when they pass through the test specimen are made congruent in direction of polarization. By making a reference and a probe light congruent in direction of polarization, it is possible to measure a polarization dependency of a nonlinear complex susceptibility as well.

The reference and probe lights that are output from the polarized light splitting Sagnac interference light path are input into a phase difference sweep mechanism. The phase difference sweep mechanism comprises a rotatable λ/4 wavelength plate and a light polarizer that makes an angle of 45° with the direction of polarization of the reference or probe light. The intensity of interference light between the reference and probe lights output from the phase difference sweep mechanism is a known function of a difference in phase and a difference in amplitude between the reference and probe lights when they are output from the polarized light splitting Sagnac type interference light path and a rotational phase difference by rotation of the λ/4 wavelength plate. The λ/4 wavelength plate is rotated to sweep a rotational phase difference and the intensity of interference light for each of rotational phase differences is measured to derive a phase difference sweep interference waveform, which is compared with the known function to find a difference in phase and a difference in amplitude between the reference and probe lights when they are output from the polarized light splitting Sagnac type interference light path, from which a nonlinear complex susceptibility can be found.

Alternatively, the phase difference sweep mechanism may comprise a λ/4 wavelength plate that makes an angle of 45° with the direction of polarization of the reference or probe light and a rotatable light polarizer. The intensity of interference light between the reference and probe lights output from the polarized light splitting Sagnac type interference light path is a known function of a difference in phase and a difference in amplitude between the reference and probe lights when they are output from the polarized light splitting Sagnac type interference light path and rotational phase difference by rotation of the light polarizer. The light polarizer is rotated to sweep a rotational phase difference and the intensity of interference light for each of rotational phase differences is measured to derive a phase difference sweep interference waveform, which is compared with the known function to find a difference in phase and a difference in amplitude between the reference and probe lights when they are output from the polarized light splitting Sagnac type interference light path, from which a nonlinear complex susceptibility can be found.

In contrast to the conventional method in which a reference and a probe light are spatially interfered with each other, these methods cause a reference and a probe light to interfere with each other in an identical beam state, namely to bring about an interference having all phase differences in the beam cross section added together. Thus, with random phase distortions within the beam cross section of a probe beam cancelled from one another, virtually ideal interference fringes can be obtained. Thus, with the analytical precision extremely enhanced, it is possible to find a true nonlinear complex susceptibility. Further, repeating the measurement by varying the timing at which the test specimen is irradiated with the excitation light allows a time resolved, nonlinear complex susceptibility of the test specimen to be measured.

BRIEF DESCRIPTION OF THE DRAWINGS

The present invention will better be understood from the following detailed description and the drawings attached hereto showing certain illustrative forms of implementation of the present invention. In this connection, it should be noted that such forms of implementation illustrated in the accompanying drawings hereof are intended in no way to limit the present invention but to facilitate an explanation and understanding thereof. In the drawings.

BEST MODES FOR CARRYING OUT THE INVENTION

Hereinafter, the present invention will be described in detail with reference to a form of implementation thereof illustrated in the drawing figures.

Figure 1:
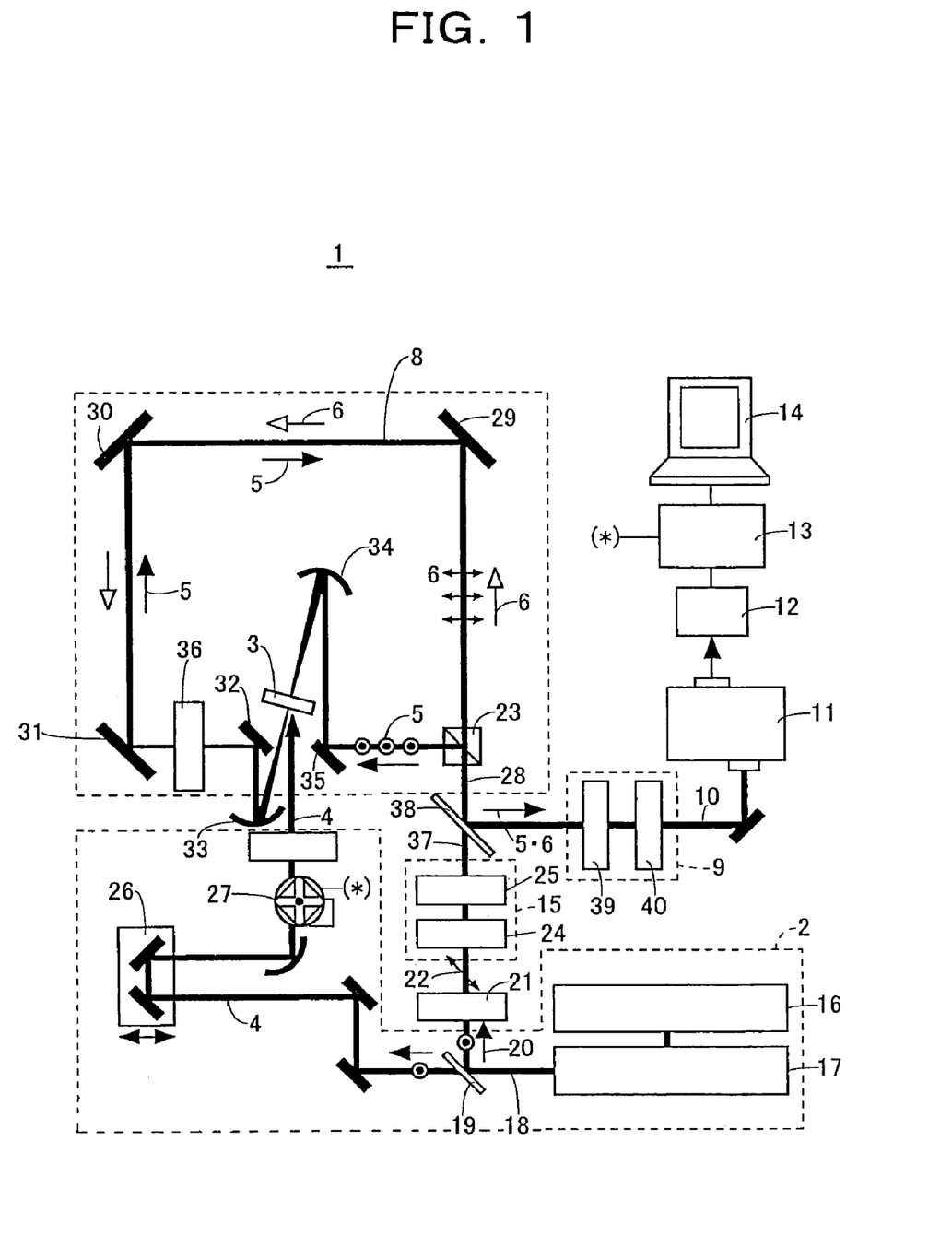
FIG. 1 is a diagram illustrating the makeup of a time resolved, nonlinear complex susceptibility measuring apparatus according to the present invention.

FIG. 1 is a diagram illustrating the makeup of a time resolved, nonlinear complex susceptibility measuring apparatus according to the present invention. As shown in the Figure, the apparatus designated by reference character 1 comprises: a light pulse light source section 2 for furnishing a light pulse; a polarized light splitting Sagnac type interference light path 8 for converting a nonlinear complex susceptibility of a test specimen 3 that is induced when the test specimen 3 is irradiated with an excitation light pulse 4 into a phase difference between a reference light 5 and a probe light 6; a phase difference sweeping mechanism 9 for sweeping the phase difference between the reference light 5 and the probe light 6 that is output from the polarized light splitting Sagnac type interference light path 8; a spectroscope 11 for spatially dispersing the wavelengths of an interference light 10 that is output from the phase difference sweeping mechanism 9; a light intensity measuring instrument 12 for measuring the intensity of an interference light component for each of the spatially dispersed wavelengths; a lock-in amplifier 13 for detecting such interference light intensities in synchronism with or relation to the timing at which the test specimen is irradiated with the excitation light pulse 4; a computer 14 for the analysis and computation of results of such measurements and for displaying a time resolved, nonlinear complex susceptibility; and a phase compensating mechanism 15 for finely adjusting the phase difference between the reference light 5 and the probe light 6.

The light pulse light source section 2 comprises a pulse generator 16 for generating light pulses; a multipath amplifier 17 for amplifying the intensity of light pulses generated by the pulse generator 16; a beam splitter 19 for splitting a light pulse 18 that is output from the multipath amplifier 17 into a light pulse 20 and an excitation light pulse 4 to supply the Sagnac type interference light path 8 with them; a light delay circuit 26 for controlling the timing of irradiation with the excitation light pulse; and a light chopper 27 for the lock-in detection. The multipath amplifier 17 is, for example, designed to output pulses having at least a half width of 30 femtoseconds and a pulse energy of about 300 µJ at an time interval (frequency) of 1 kHz.

A light pulse 20 to be supplied into the polarized light splitting Sagnac type interference light path 8 is passed through a light polarizer 21 to become a linearly polarized light 22 and then incident on the phase compensating mechanism 15. The phase compensating mechanism 15 is used to compensate for and make zero a fixed phase that may be caused between a reference light 5 and a probe light 6 when the reference light 5 or the probe light 6 is reflected by or refracted through a polarized light beam splitter 23 composing a part of the polarized light splitting Sagnac type interference light path 8.

The phase difference compensating mechanism 15 comprises a $\lambda/2$ wavelength plate 24 that can be rotated as desired about its optical axis and a $\lambda/4$ wavelength plate 25 having its fast or slow axis fixed at an angle of 45° relative to a direction of polarization of the reference light 5 or the probe light 6 and is provided to establish a desired phase difference between the reference light 5 and the probe light 6 by adjusting the angle of rotation of the $\lambda/2$ wavelength plate 24.

Figure 2:
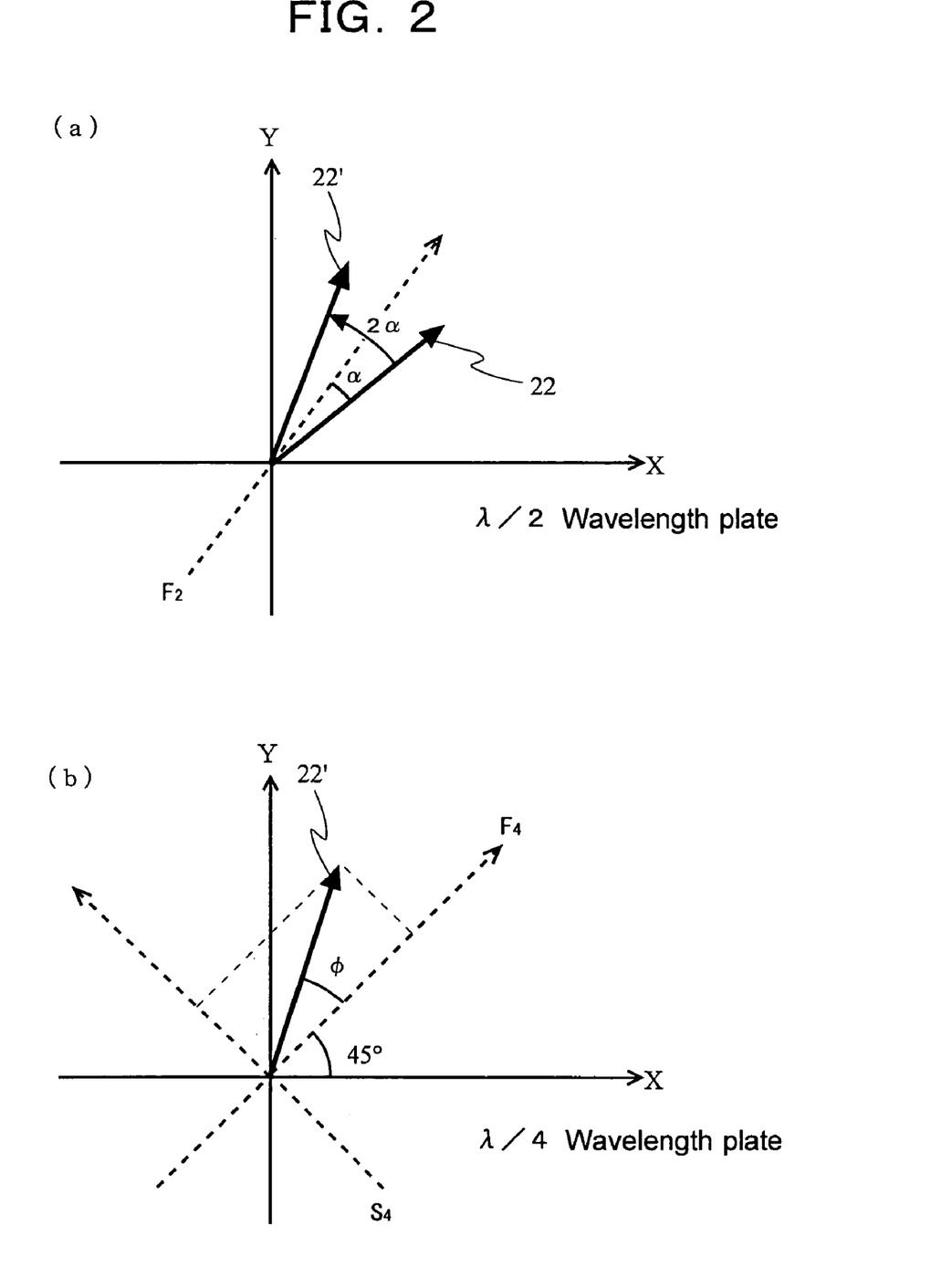
FIG. 2 diagrammatically shows operations of a phase difference compensating mechanism comprising a $\lambda/2$ wavelength plate and $\lambda/4$ wavelength plate.

Next, mention is made of how the phase difference compensating mechanism 15 operates. FIG. 2 illustrates how the phase difference compensating mechanism made of the $\lambda/2$ and $\lambda/4$ wavelength plates operates wherein FIG. 2(a) illustrates how the $\lambda/2$ wavelength plate operates. In the Figure, the $\lambda/2$ wavelength plate 24 has the fast axis indicated by broke line $F_2$, which makes an angle of α with the incident linearly polarized light 22. The reference and probe lights 5 and 6 are polarized in directions of X and Y axes, respectively, to form their respective polarized lights. The function of the $\lambda/2$ wavelength plate is to invert the incident linearly polarized light as it is linearly polarized, symmetrically about the fast axis $F_2$ of the $\lambda/2$ wavelength plate 24. Thus, the incident linearly polarized light 22 is allowed to appear as a linearly polarized- light 22' that is inclined at an angle of $2\alpha$ from the direction of polarization in which it is incident. To wit, rotating the fast axis F2 of the $\lambda/2$ wavelength plate 24 (changing the $\alpha$) allows the direction of polarization of the incident linearly polarized light 22 to be reoriented in a desired direction.

FIG. 2(*b*) is a diagram illustrating a relationship in orientation of the linearly polarized light 22' whose direction of polarization is reoriented in a desired direction by rotating the $\lambda/2$ wavelength plate 24, with a fast and a slow axis $F_4$ and $S_4$ of the $\lambda/4$ wavelength plate 25. It is shown that the fast and slow axes $F_4$ and $S_4$ make an angle of 90° with each other and that the fast axis $F_4$ is fixed at an angle of 45° to the X direction (in which the reference light 5 is polarized). Assuming that the linearly polarized light 22 makes an angle of $\phi$ with the fast axis $F_4$, the linearly polarized light 22' has an amplitude E, a frequency $\omega$, a propagation constant k and a propagation direction z and time is t, the component $E_f$ to the fast axis $F_4$ of the linearly polarized light 22' can be expressed by $$E_f = E \cos\phi \cos(\omega t - kz) \quad (1)$$

and the component $E_s$ to the slow axis $S_4$ of the linearly polarized light 22' can be expressed by $$E_s = E \sin\phi \cos(\omega t - kz) \quad (2)$$

Since the $\lambda/4$ wavelength plate produces a phase difference of $\pi/2$ between the polarized light component to the fast axis and the polarized light component to the slow axis, if the phase advanced component $E_f'$ past the $\lambda/4$ wavelength plate 25 is:

$$E_f' = E \cos\phi \cos(\omega t - kz) \quad (3),$$

then the phase delayed component $E_s'$ becomes:

$$\begin{aligned} E_s' &= E \sin\varphi \cos(\omega t - kz - \pi/2) \\ &= E \sin\varphi \sin(\omega t - kz). \end{aligned} \quad (4)$$

If the phase advanced and delayed components $E_f'$ and $E_s'$ past the $\lambda/4$ wavelength plate 25 are decomposed into their respective X-axial and Y-axial components, the X-axial component $E_x'$ will be:

$$\begin{aligned} E_x' &= 1/\sqrt{2}\, E \cos\varphi \cos(\omega t - kz) \\ &\quad - 1/\sqrt{2}\, E \sin\varphi \sin(\omega t - kz) \\ &= 1/\sqrt{2}\, E \cos(\omega t - kz + \varphi) \end{aligned} \quad (5)$$

and the Y-axis component $E_y'$ will be:

$$\begin{aligned} E_y' &= 1/\sqrt{2}\, E \cos\varphi \cos(\omega t - kz) \\ &\quad + 1/\sqrt{2}\, E \sin\varphi \sin(\omega t - kz) \\ &= 1/\sqrt{2}\, E \cos(\omega t - kz - \varphi). \end{aligned} \quad (6)$$

As is apparent from the equations (5) and (6), a phase difference of $2\phi$ comes to be between the X-axial and Y-axial components. To wit, rotating the $\lambda/2$ wavelength plate by any angle $\phi$ allows adjusting the phase difference between the X-axial and Y-axial components at any corresponding value, thereby compensating for and making zero a fixed phase that may be produced between the reference and probe lights by any unavoidable cause such as reflection or refraction.

Mention is next made of the makeup of the polarized light splitting Sagnac type interference light path with reference to FIG. 1. The polarized light splitting Sagnac type interference light path 8 comprises the polarized light beam splitter 23 for splitting an incident linear polarized light into a reference light 5 and a probe light 6; a plurality of mirrors 29-35 arranged so that the reference and probe lights 5 and 6 propagate through the same path in opposite directions and are then combined together at the beam splitter 23 into a single unitary beam; and a $\lambda/2$ wavelength plate 36 disposed in the optical path 8.

The polarized light beam splitter 23 splits an incident linearly polarized light 28 into a light polarized in a direction (X-axis direction) in a plane perpendicular to the sheet of drawing in the Figure, namely a reference light 5 and a light polarized in a direction (Y-axis direction) in a plane parallel to the sheet of drawing in the Figure, namely a probe light 6. The reference and probe lights 5 and 6 propagate through the Sagnac type interference light path 8 clockwise and counterclockwise, respectively, in the Figure.

The $\lambda/2$ wavelength plate 36 makes the reference and probe lights 5 and 6 congruent in direction of polarization when they pass through a test specimen 3. To wit, in the Figure the probe light 6 (polarized in the Y direction) when passing though the $\lambda/2$ wavelength plate 36 rotates its direction of polarization by an angle of 90° to the X direction and then is incident on the test specimen 3. Then, since the reference light 5 as it remains polarized in the X direction is incident on the test specimen 3, the reference and probe lights 5 and 6 when they pass through the test specimen 3 are made congruent in direction of polarization. With the reference and probe lights 5 and 6 made congruent there in direction of polarization, it becomes possible to measure tensor components of a nonlinear complex susceptibility.

Mention is next made of how the polarized light splitting Sagnac type interference light path operates with reference to FIG. 1. An input light pulse 37 that is output from the phase compensating mechanism 15 transmits through the beam splitter 38 that separates an input light pulse 28 feeding to the polarized light splitting Sagnac type interference light path 8 and light pulses 5 and 6 output from the polarized light splitting Sagnac type interference light path 8, the input light pulse 28 then entering the polarized light beam splitter 23 in the polarized light splitting Sagnac type interference light path 8. The input light pulse 28 is split by the polarized light beam splitter 23 into a reference and a probe light 5 and 6 propagating through the Sagnac type interference light path 8 clockwise and counterclockwise, respectively. Since the length of the optical path for the reference light 5 to travel to reach the test specimen 3 is shorter than that for the probe light 6 to travel to reach the test specimen 3, the reference light 5 first reaches the test specimen and the probe light 6 later reaches the test specimen 3. Controlling the operation of the light delay unit 26 so that the test specimen 3 is irradiated with an excitation light pulse 4 in a time interval between the time instant at which the reference light 5 reaches the test specimen 3 and the time instant at which the probe light 6 reaches the test specimen 3 allows the reference light 5 to pass through the test specimen 3 in an unexcited state and the probe light 6 to pass through the test specimen 3 in an excited or excitation relaxing state or while it is relaxing. Since the test specimen 3 in an excited or excitation relaxing state involves its nonlinear complex susceptibility, the probe light 6 affected by the nonlinear complex susceptibility undergoes a change in phase and amplitude. Since the polarized light splitting Sagnac type interference light path 8 has its clockwise and counter clockwise optical paths exactly the same, the reference and probe lights 5 and 6 issuing from the polarized beam splitter 23 have differences in phase and amplitude imparted corresponding to the nonlinear complex susceptibility. Moreover, controlling the operation of the light delay unit 26 allows changing the time at which the specimen 3 is irradiated with the probe light 6, it is possible to measure a temporal change in nonlinear complex susceptibility from the time of initiation of an excited state to the time of its ending.

Mention is next made of the phase difference sweeping mechanism. As shown in FIG. 1, the reference and probe lights 5 and 6 output from the polarized light splitting Sagnac type interference light path 8 are input into the phase difference sweeping mechanism 9.

Mention is first made of a first embodiment of the phase difference sweeping mechanism. As shown in FIG. 1, the first embodiment of the phase difference sweeping mechanism 9 comprises a rotatable $\lambda/4$ wavelength plate 39 and a light polarizer 40 having an angle of 45° made to the direction of polarization of the reference light 5 (or the probe light 6) such that rotating the $\lambda/4$ wavelength plate 39 allows changing the difference in phase between the reference and probe lights 5 and 6 as desired. To wit, the difference in phase between the reference and probe lights 5 and 6 can be swept. The intensity of interference light between the reference and probe lights 5 and 6 output from the phase difference sweeping mechanism 9 is represented as a known function of differences in phase and amplitude between the reference and probe lights 5 and 6 when output from the polarized light splitting Sagnac type interference light path 8 and a rotational phase difference between them by the rotation of the $\lambda/4$ wavelength plate 39.

Figure 3:
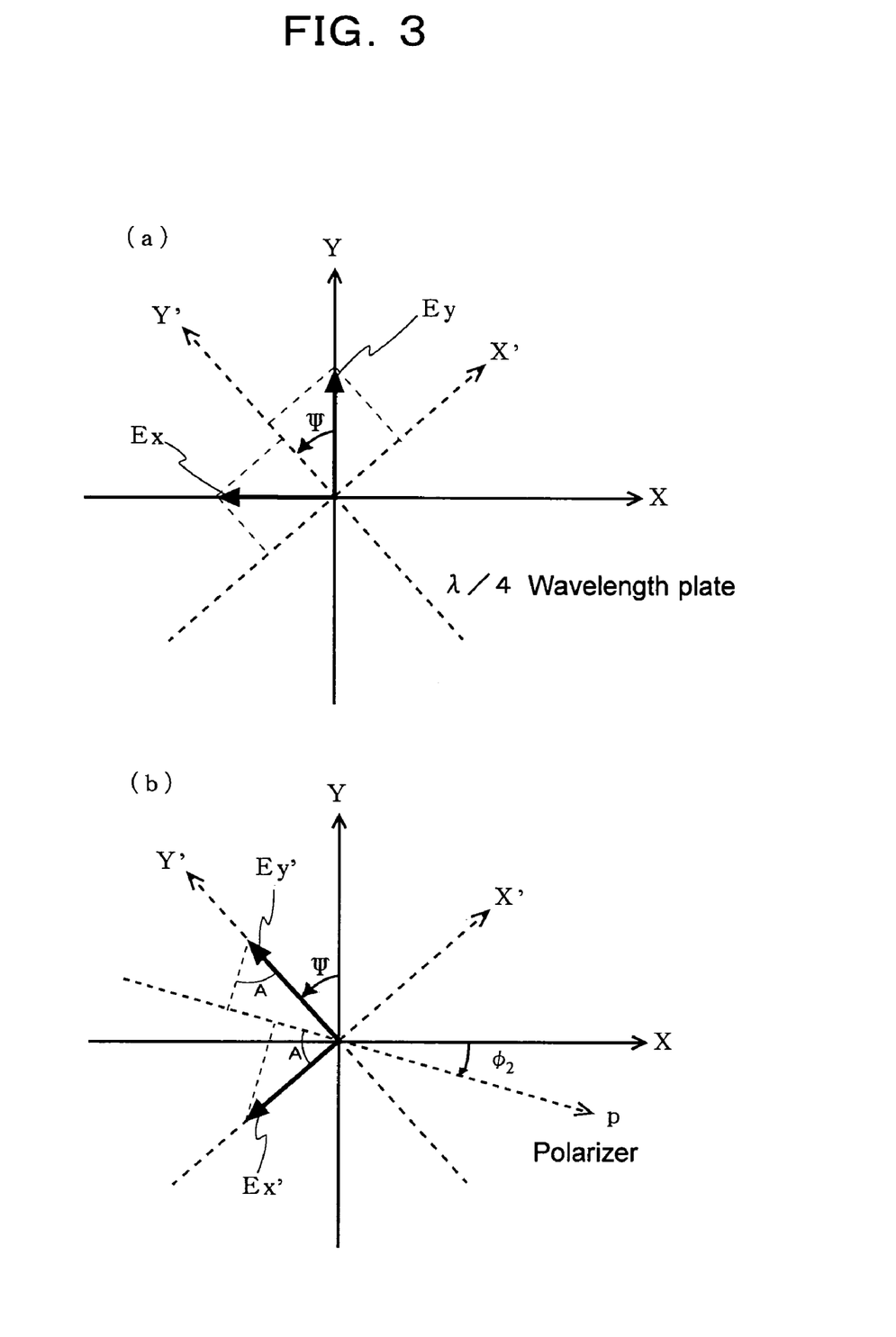
FIG. 3 diagrammatically shows operations of a phase difference sweeping mechanism comprising a $\lambda/4$ wavelength plate and a light polarizer in its first form of implementation.

Mention is next made of how the phase difference sweeping mechanism according to its first embodiment operates. FIG. 3 graphically shows operations of the phase difference sweeping mechanism comprising the $\lambda/4$ wavelength plate and the polarizer in accordance with its first embodiment. FIG. 3(a) is a diagram illustrating a relationship in orientation of a reference and a probe light Ex and Ey which are incident on the $\lambda/4$ wavelength plate, and a slow and a fast axis X' and Y' of the $\lambda/4$ wavelength plate. It is assumed that Ψ represents an angle that the probe light Ey makes with the fast axis Y', namely an angle of rotation of the $\lambda/4$ wavelength plate, and that θ represents the phase difference between the reference and probe lights 5 and 6 when output from the polarized light splitting Sagnac type interference light path 8. Assuming that $E_{ref}$ and $E_{pro}$ represent the amplitudes of the reference and probe lights, respectively, the reference and probe lights Ex and Ey can be expressed, respectively, by $$E_x = E_{ref} \exp\{i(kx-\omega t)\} \tag{7}$$

and $$E_y = E_{pro} \exp\{i(kx-\omega t)\} \cdot \exp(i \cdot \theta) \tag{8}$$

Then, since the $\lambda/4$ wavelength plate produces a phase difference of π/2 between the fast and slow polarized light components, the polarized light component Ey' of the fast axis Y' and the polarized light component Ex' of the slow axis X' past the $\lambda/4$ wavelength plate can be expressed respectively, by $$\begin{aligned} E_y' &= E_y \cos \Psi + E_x \sin \Psi \\ &= [E_{pro} \exp\{i\theta\}\cos \Psi + E_{ref} \sin \Psi]\exp\{i(kx-\omega t)\} \end{aligned} \tag{9}$$

and $$\begin{aligned} E_x' &= [E_y \sin \Psi - E_x \cos \Psi] \cdot \exp\{i \cdot \pi/2\} \\ &= i \cdot [E_{pro} \cdot \exp(i \cdot \theta)\sin \Psi - E_{ref} \cos \Psi] \cdot \exp\{i(kx-\omega t)\}. \end{aligned} \tag{10}$$

FIG. 3(b) is a diagram illustrating a relationship in orientation of the polarized light component Ey' of the fast axis Y' and the polarized light component Ex' of the slow axis X' past the $\lambda/4$ wavelength plate and the light polarizer wherein $\phi_2$ indicates an angle that the direction of the reference light (X) makes with the transmission axis of the polarizer (p).

The light polarizer acts to output only components in the transmission axis p of the polarized light component Ey' of the fast axis Y' and the polarized light component Ex' of the slow axis X'. For example, if $E_{ref}=E_{pro}=E$, from the equations (9) and (10) the light component $E_p$ that transmits through the polarizer is found as $$\begin{aligned} E_p &= -E_y' \sin A - E_x' \cos A \\ &= -E[(\sin \Psi \sin A - i\cos\Psi\cos A) \\ &\quad + \exp\{i\theta\}(\cos \Psi \sin A + i\sin \Psi \cos A)] \end{aligned} \tag{11}$$

(where $E_{ref}=E_{pro}\equiv E$ and $A=\Psi+\phi_2$.) Further, since the intensity of interference light formed past the polarizer is a square of the absolute value of $E_p$, it follows that:

$$\begin{aligned} |E_p|^2 &= E_p \cdot E_p^* \\ &= E^2[(\sin \Psi \sin A - i\cdot\cos \Psi \cos A) + \\ &\quad \exp\{i\cdot\theta\}\cdot(\cos \Psi \sin A + i\cdot\sin \Psi \cos A)] \times \\ &\quad [(\sin \Psi \sin A + i\cdot\cos \Psi \cos A) + \\ &\quad \exp\{-i\cdot\theta\}\cdot(\cos \Psi \sin A - i\cdot\sin \Psi \cos A)] \end{aligned} \tag{12}$$

Further, this equation can be edited as follows:

$$\begin{aligned} |E_p|^2 &= E^2[1 - (e^{-i\theta} + e^{i\theta})\sin\Psi\cos\Psi\cos 2A + \\ &\quad i\cdot\sin A\cos A(e^{-i\theta} - e^{i\theta})] \\ &= E^2[1 - 2\cos\theta\sin\Psi\cos\Psi\cos 2A - \\ &\quad i\cdot\sin A\cos A\cdot(-2i\sin\theta)] \\ &= E^2[1 - \sin 2\Psi\cos 2A\cos\theta - \sin 2A\sin\theta] \\ &= E^2[1 - \sin 2\Psi\cos(2\Psi + 2\phi_2)\cos\theta - \\ &\quad \sin(2\Psi + 2\phi_2)\sin\theta] \end{aligned} \tag{13}$$

As can be seen from the equation (13), the intensity of interference light $|E_p|^2$ is a function of the phase difference θ that pre-exists between the reference and probe lights and the angle of rotation Ψ of the $\lambda/4$ wavelength plate. At least, if the intensity of interference light $|E_p|^2$ and the angle of rotation $\Psi$ are known, $\theta$ can be found from the equation (13). Further preferably, $\theta$ can be found with greater precision from a phase difference swept interference waveform measured by sweeping $\Psi$ and then by way of the technique of curve fitting.

While the explanation for the sake of rendering it easier to understand was made as for $E_{ref}=E_{pro}=E$ which allows analytical representation, where $E_{ref} \neq E_{pro}$, phase difference swept interference waveforms for various $E_{ref}/E_{pro}$ ratios and $\theta$ can be found in advance by numerical calculation and compared with a measured phase difference interference waveform. This permits both a phase difference and an amplitude ratio that pre-exist between the reference and probe lights to be found easily and then allows finding a nonlinear complex susceptibility from these phase difference and amplitude ratio.

In this way, it is possible to sweep the rotational phase difference by rotating the $\lambda/4$ wavelength plate 39, to measure the intensity of interference light for each of rotational phase differences with the light intensity measuring unit 12 to find a phase difference swept waveform, to compare the same with a known functional one to find a phase difference and an amplitude ratio between a reference and a probe lights 5 and 6 when output from the polarized light splitting Sagnac type interference light path 8 and then to obtain a nonlinear complex susceptibility from the phase difference and amplitude ratio. Also, dispersing wavelengths with the spectroscope 11 and measuring the intensity of interference light for each of the wavelengths dispersed allows obtaining a nonlinear complex susceptibility for each of the wavelengths. In contrast to the conventional method in which a reference and a probe light are spatially interfered with each other, this method causes a reference and a probe light to interfere with each other in an identical beam state, namely to bring about an interference having all phase differences in the beam cross section added together. Thus, with random phase distortions within the beam cross section of a probe beam cancelled from one another, virtually ideal interference fringes can be obtained. Thus, with the analytical precision extremely enhanced, it is possible to find a true nonlinear complex susceptibility.

Mention is next made of a second embodiment of the phase difference sweeping mechanism. The second embodiment as in the first embodiment comprises a $\lambda/4$ wavelength plate and a light polarizer, but differs from the first embodiment in that the angle of rotation of the $\lambda/4$ wavelength plate is fixed and the polarizer is rotated.

Figure 4:
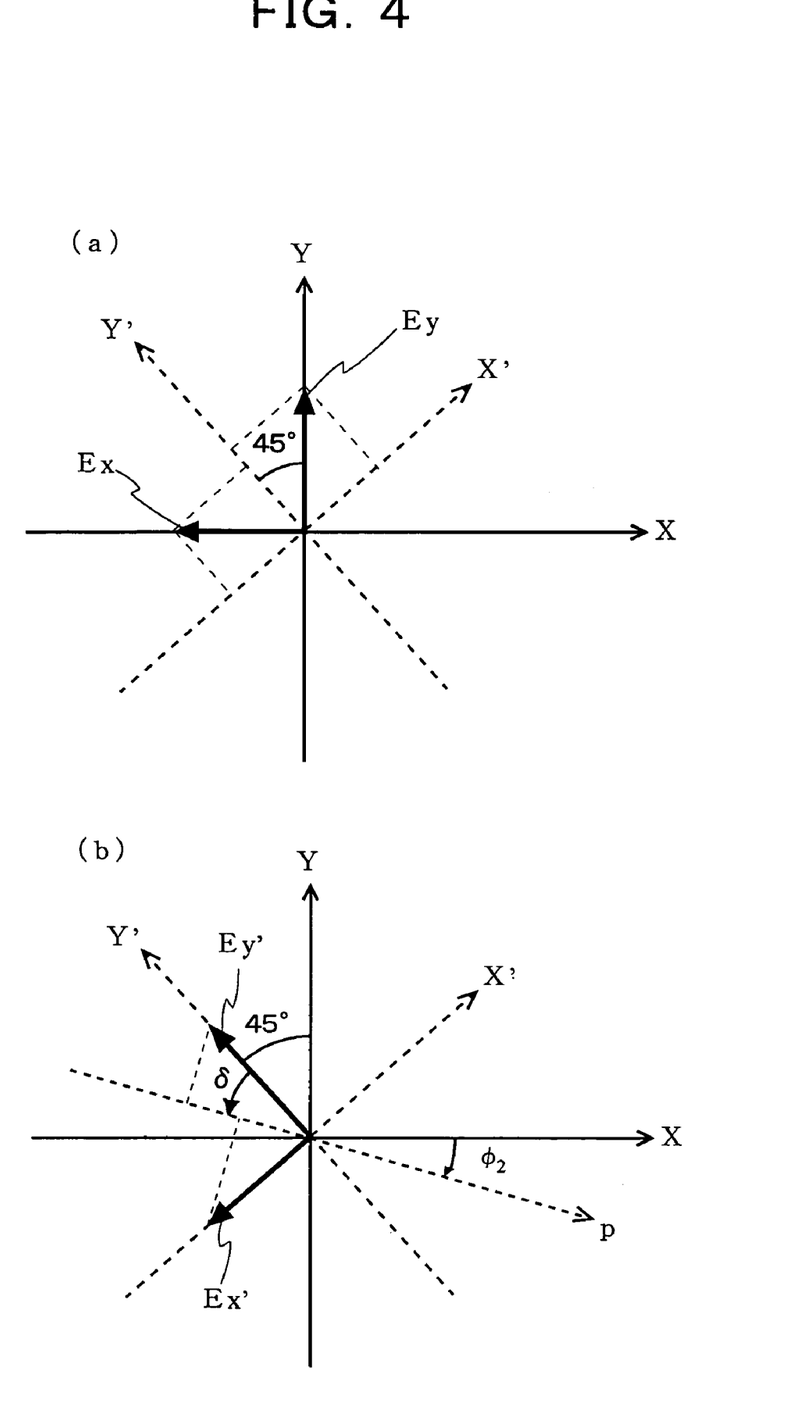
FIG. 4 diagrammatically shows operations of a phase difference sweeping mechanism in its second form of implementation.

FIG. 4 diagrammatically shows operations of a phase difference sweeping mechanism of its second embodiment. FIG. 4(*a*) is a diagram illustrating a relationship in orientation of a reference and a probe light Ex and Ey which are incident on the $\lambda/4$ wavelength plate and a fast and a slow axis X' and Y' of the $\lambda/4$ wavelength plate. The angle $\Psi$ that the probe light Ey makes with the fast axis Y' is fixed at 45°.

In this case, the polarized light component Ey' of the fast axis and the polarized light component Ex' of the slow axis past the $\lambda/4$ wavelength plate, corresponding to the equations (9) and (10), can be expressed, respectively, by $$E'_y = \frac{1}{\sqrt{2}}[E_{pro} \cdot \exp\{i\theta\} + E_{ref}] \quad (14)$$

and $$E'_x = \frac{i}{\sqrt{2}}[E_{pro} \cdot \exp\{i\theta\} - E_{ref}] \quad (15)$$

(Hereafter, equations will be shown by omitting the common phase term: $\exp\{i(kx-\omega t)\}$.)

Further, FIG. 4(*b*) is a diagram illustrating a relationship in orientation of the polarized light component Ey' of the fast axis and the polarized light component Ex' of the slow axis past the $\lambda/4$ wavelength plate with the polarizer. In the Figure, the angle that the polarized light component Ey' of the fast axis makes with direction of polarization (-p) of the polarizer is assumed to be $\delta$. As is apparent from the Figure, $\delta = \pi/4 - \phi_2$, and a rotation of the polarizer (to change $\phi_2$) corresponds to a change in $\delta$.

The light component $E_p$ that transmits through the polarizer is expressed from the equations (14) and (15) as follows:

$$E_p = -\frac{1}{\sqrt{2}}[E_{pro} \exp\{i\theta\} \cdot \exp\{i\delta\} + E_{ref} \cdot \exp\{-i\delta\}]. \quad (16)$$

Further, since the intensity of interference light formed past the polarizer is a square of the absolute value of $E_p$, $$|E_p|^2 = E_p \cdot E_p^* \quad (17)$$
$$= \frac{1}{2}[E_{pro}^2 + E_{ref}^2 + 2E_{pro} \cdot E_{ref} \cdot \cos(2\delta + \theta)].$$

Figure 5:
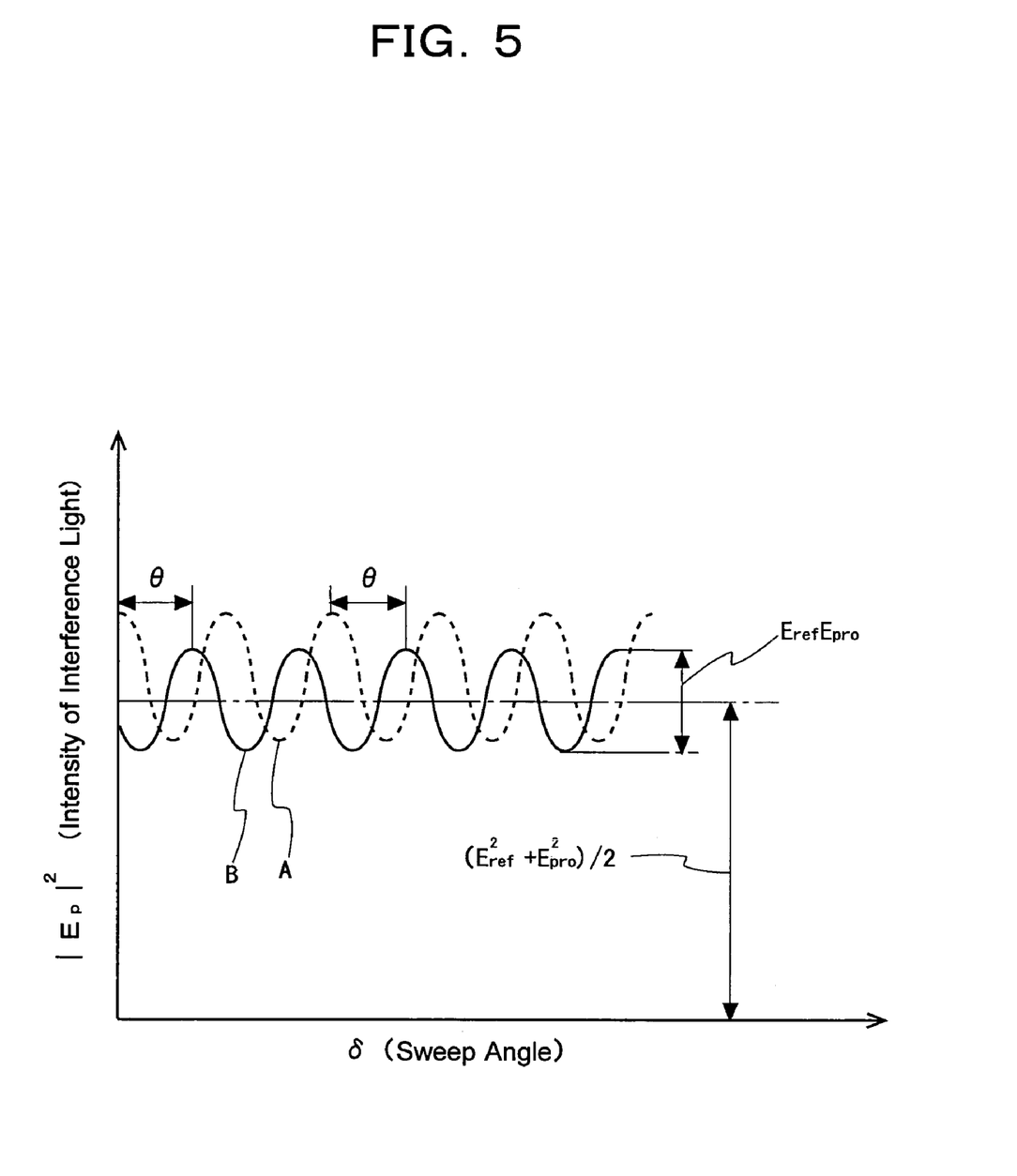
FIG. 5 is a graph showing results of measuring a phase difference θ which reflects a nonlinear complex susceptibility.

FIG. 5 is a graph showing results of measuring a phase difference $\theta$ which reflects a nonlinear complex susceptibility. In the graph, the ordinate axis represents the intensity of interference light $|E_p|^2$ that is expressed by the equation (17) and the abscissa axis represents the angle of rotation $\delta$ of the polarizer. A periodic function A represents an output where there is no excitation light pulse 4 irradiated and a periodic function B represents an output where there is an excitation light pulse 4 irradiated. Since the periodic function A does not contain $\theta$ as is apparent from the equation (17), measuring a deviation in phase between the periodic functions A and B as shown in the Figure allows a phase $\theta$ corresponding to a nonlinear complex susceptibility to be measured. Also, in this case, since it suffices to measure a deviation in relative phase between the periodic functions A and B, there is no need to compensate for a fixed phase between the reference and probe lights, thereby permitting the phase difference compensating mechanism to be omitted.

Further, if both phase and amplitude change simultaneously with a nonlinear complex susceptibility, it is possible to measure changes in phase and amplitude easily. For example, if a probe light changes its amplitude from $E_{pro}$ to $E_{pro}+\Delta E$ and its phase from $\theta$ to $\theta+\Delta\theta$, namely the probe light Ey is expressed by $$E_{pro}'=(E_{pro}+\Delta E)\cdot\exp\{i\Delta\theta\} \quad (18),$$

using the equation (18) in place of the equation (14) allows the intensity of interference light $|E_p'|^2$ formed past the polarizer to be expressed by $$|E'_p|^2 = \frac{1}{2}[E_{ref}^2 + (E_{pro} + \Delta E)^2 + 2E_{ref}(E_{pro} + \quad (19)$$
$$\Delta E)\cos\{(2\delta - \theta - \Delta\theta)\}]$$
$$\approx \frac{1}{2}[E_{ref}^2 + E_{pro}^2 + 2E_{pro}\Delta E +$$
$$2E_{ref}(E_{pro} + \Delta E)\{\cos(2\delta - \theta)\cos(\Delta\theta) + \sin(2\delta - \theta)\sin(\Delta\theta)\}]$$
$$\approx \frac{1}{2}[E_{ref}^2 + E_{pro}^2 + 2E_{ref}E_{pro}\cos(2\delta - \theta) + 2E_{pro}\Delta E +$$
$$2E_{ref}\Delta E \cos(2\delta - \theta) + 2E_{ref}E_{pro}\Delta\theta \sin(2\delta - \theta)]$$

Thus, assuming the differential signal in the intensity of interference light before and after the change to be $\Delta I$, it follows that:

$$\Delta I \approx E_{ref}\Delta E\{1 + \cos(2\delta - \theta)\} + E_{ref}E_{pro}\Delta\theta\sin(2\delta - \theta) \quad (20)$$

and from this equation, both the phase $\Delta\theta$ and amplitude change $\Delta E$ can be found simultaneously.

Mention is next made of a specific example.

Figure 6:
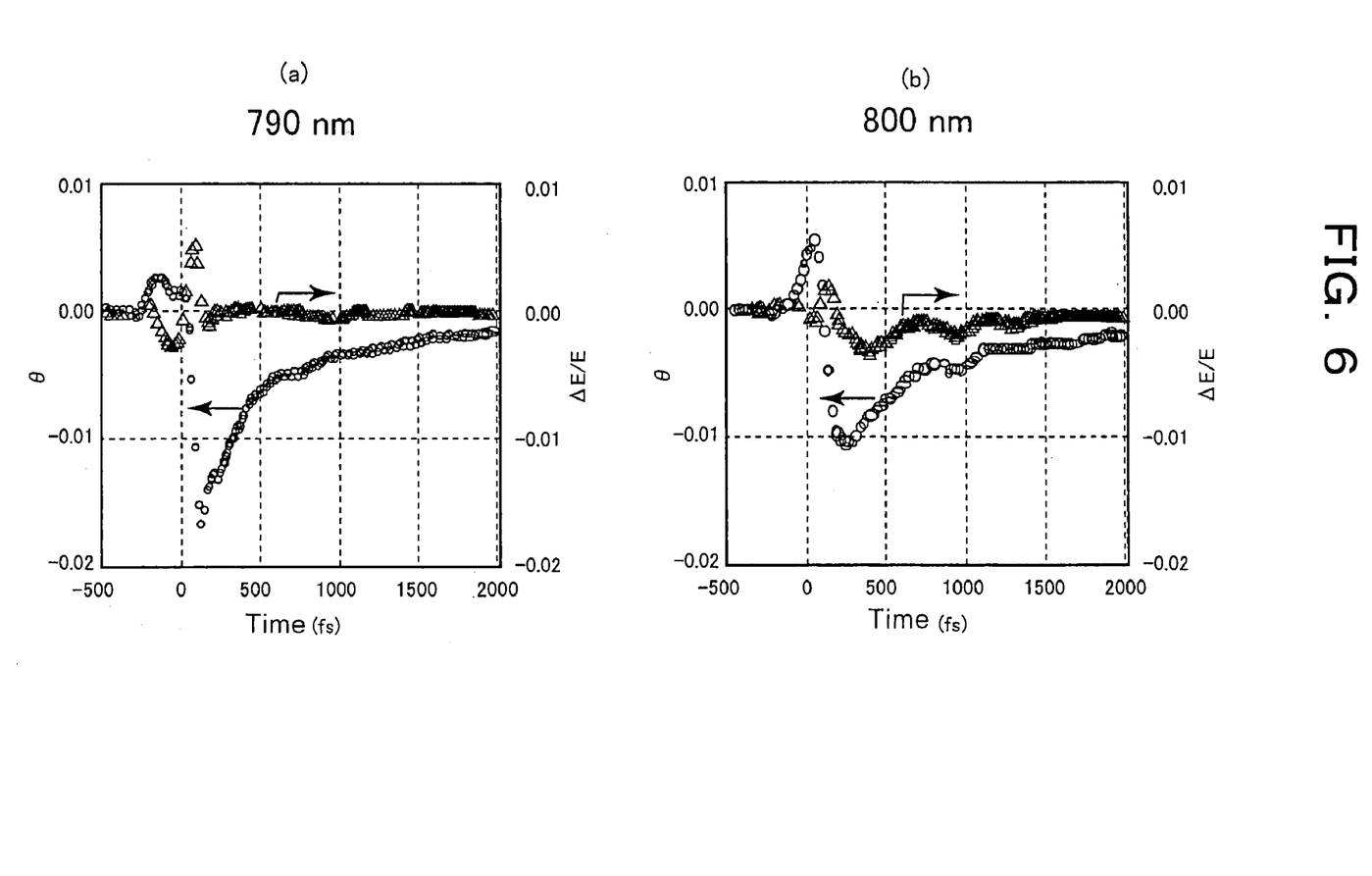
FIG. 6 graphically shows results of measurement on carbon disulfide by the time resolved, nonlinear complex susceptibility measuring apparatus of the present invention.

FIG. 6 graphically shows results of measurement on carbon disulfide by the time resolved, nonlinear complex susceptibility measuring apparatus of the present invention. In each graph, the ordinate axis at the left hand side represents the phase difference $\theta$ based on the nonlinear optical effect and the ordinate axis at the right hand side represents the amplitude change $\Delta E/E$ while the abscissa axis represents time (fs) starting with the time instant of irradiation with an excitation light pulse. FIG. 6(a) shows an instance that the reference and probe lights have a wavelength of 790 nm and FIG. 6(b) shows an instance that they have a wavelength of 800 nm. The excitation light pulse had a pulse width of about 10 fs. From these Figures, it is seen that the phase difference $\theta$ and the amplitude change $\Delta E/E$ are relaxed over a long time period after the excitation. From changes in these phase difference $\theta$ and amplitude change $\Delta E/E$ with time, there can be found the relaxation property of a nonlinear complex susceptibility.

While in the foregoing explanation the $\lambda/2$ and $\lambda/4$ wavelength plates are shown as used so that they can be rotated about their optical axes to control the phase difference between proper polarized lights, it should be apparent, of course, that they may be replaced with an electrooptic crystal formed with electrodes so that controlling the voltage applied across them controls the same.

As will be appreciated from the foregoing description, the apparatus of the present invention that uses a pair of polarized lights into which a single light pulse is split as a reference and a probe light orthogonal to each other allows sweeping the phase difference between the reference and probe lights, and its ability to sweep the phase difference allows measuring a sweep waveform for the phase difference. Then, since the reference and probe lights are interfered with each other in a single beam state, the measurement can be made unaffected by any distortion of the wave front of a probe light, and a phase difference sweep waveform having a virtually ideal sinusoidal waveform can be obtained. This permits precise measurement of a time resolved, nonlinear complex susceptibility. Also, including a $\lambda/2$ wavelength plate in a Sagnac type interference light path allows measuring a direction of polarization dependency of the nonlinear complex susceptibility as well. Further, including a phase compensating mechanism in the apparatus allows enhancing the precision of measurement.

What is claimed is:

1. A time resolved, nonlinear complex susceptibility measuring apparatus having: a Sagnac type interference light path in which a reference and a probe light to propagate, a light pulse light source for providing a light pulse with which to irradiate a test specimen disposed in the light path and for supplying the Sagnac type interference light path with a light pulse, and a measuring instrument for measuring the intensity of interference light between the reference and probe lights, characterized in that:

the reference and probe lights are a pair of polarized lights orthogonal to each other, and the Sagnac type interference light path is a polarized light splitting Sagnac type interference light path, and that the apparatus includes:

a direction of polarization converting mechanism for rotating a direction of polarization of the reference and probe lights by an angle of 90° in the polarized light splitting Sagnac type interference light path;

a phase difference sweep mechanism for sweeping a phase difference between the reference and probe lights that are output from the polarized light splitting Sagnac type interference light path; and a phase difference compensating mechanism for compensating for a phase difference between the reference and probe lights prior to entry of the light pulse into the polarized light splitting Sagnac type interference light path, whereby a phase difference between the reference and probe lights that are output from the polarized light Sagnac type interference light path is swept and a time resolved, nonlinear complex susceptibility is found from a phase difference sweep interference waveform obtained by measuring the intensity of interference light between the reference and probe lights for each of such phase differences swept.

2. A time resolved, nonlinear complex susceptibility measuring apparatus as set forth in claim 1, characterized in that the phase difference compensating mechanism for compensating for a phase difference between the reference and probe lights comprises a $\lambda/2$ and a $\lambda/4$ wavelength plate disposed between the polarized light splitting Sagnac type interference light path and the light pulse light source for supplying the light path with the light pulse whereby rotating the $\lambda/2$ wavelength plate allows compensating for a phase difference between the reference and probe lights.

3. A time resolved, nonlinear complex susceptibility measuring apparatus as set forth in claim 1, characterized in that the direction of polarization converting mechanism for rotating a direction of polarization of the reference and probe lights by an angle of 90° in the polarized light splitting Sagnac type interference light path comprises a $\lambda/2$ wavelength plate disposed in the light path.

4. A time resolved, nonlinear complex susceptibility measuring apparatus as set forth in claim 1, characterized in that the phase difference sweep mechanism for sweeping a phase difference between the reference and probe lights that are output from the polarized light splitting Sagnac type interference light path comprises a $\lambda/4$ wavelength plate and a light polarizer which are disposed between an output end of the polarized light splitting Sagnac type interference light path and the measuring instrument for measuring the intensity of interference light between the reference and probe lights whereby rotating the $\lambda/4$ wavelength plate allows sweeping a phase difference between the reference and probe lights.

5. A time resolved, nonlinear complex susceptibility measuring apparatus as set forth in claim 1, characterized in that the phase difference sweep mechanism for sweeping a phase difference between the reference and probe lights that are output from the polarized light splitting Sagnac type interference light path comprises a $\lambda/4$ wavelength plate and a light polarizer which are disposed between an output end of the polarized light splitting Sagnac type interference light path and the measuring instrument for measuring the intensity of interference light between the reference and probe lights whereby rotating the light polarizer allows sweeping a phase difference between the reference and probe lights.

6. A time resolved, nonlinear complex susceptibility measuring apparatus having: a Sagnac type interference light path in which a reference light and a probe light to propagate, a light pulse light source for providing a light pulse with which to irradiate a test specimen disposed in the light path and for supplying the Sagnac type interference light path with a light pulse, and a measuring instrument for measuring the intensity of interference light between the reference and probe lights, characterized in that:

the reference and probe lights are a pair of polarized lights orthogonal to each other, and the Sagnac type interference light path is a polarized light splitting Sagnac type interference light path, and that the apparatus includes:

a direction of polarization converting mechanism for rotating a direction of polarization of the reference and probe lights by an angle of 90° in the polarized light splitting Sagnac type interference light path;

a phase difference sweep mechanism for sweeping a phase difference between the reference and probe lights that are output from the polarized light splitting Sagnac type interference light path, wherein the phase difference sweep mechanism comprises a $\lambda/4$ wavelength plate and a light polarizer which are disposed between an output end of the polarized light splitting Sagnac type interference light path and the measuring instrument for measuring the intensity of interference light between the reference and probe lights wherein rotating the light polarizer allows sweeping a phase difference between the reference and probe lights; and wherein a phase difference between the reference and probe lights that are output from the polarized light Sagnac type interference light path is swept and a time resolved, nonlinear complex susceptibility is found from a phase difference sweep interference waveform obtained by measuring the intensity of interference light between the reference and probe lights for each of such phase differences swept.

* * * * *